(12) United States Patent
Asfora

(10) Patent No.: US 7,666,208 B1
(45) Date of Patent: Feb. 23, 2010

(54) POSTERIOR CERVICAL VERTEBRAL STABILIZING SYSTEM

(75) Inventor: Wilson T. Asfora, Sioux Falls, SD (US)

(73) Assignee: Asfora IP, LLC, Sioux Falls, SD (US)

( * ) Notice: Subject to any disclaimer, the term of this patent is extended or adjusted under 35 U.S.C. 154(b) by 78 days.

(21) Appl. No.: 11/120,522

(22) Filed: Apr. 29, 2005

(51) Int. Cl.
*A61B 17/70* (2006.01)

(52) U.S. Cl. ..................................... 606/249

(58) Field of Classification Search ... 623/17.11–17.16; 606/61, 69–71, 248, 249
See application file for complete search history.

(56) References Cited

U.S. PATENT DOCUMENTS

| | | | |
|---|---|---|---|
| 4,369,769 A | | 1/1983 | Edwards |
| 4,570,618 A | | 2/1986 | Wu |
| 4,604,995 A | | 8/1986 | Stephens et al. |
| 4,836,193 A | * | 6/1989 | Ransford ............... 606/61 |
| 5,306,275 A | | 4/1994 | Bryan |
| 5,413,576 A | | 5/1995 | Rivard |
| 5,725,582 A | | 3/1998 | Bevan et al. |
| 5,733,284 A | | 3/1998 | Martin |
| 5,879,385 A | * | 3/1999 | Crockard et al. ......... 623/17.11 |
| RE36,221 E | | 6/1999 | Breard et al. |
| 5,928,232 A | | 7/1999 | Howland et al. |
| 6,190,387 B1 | | 2/2001 | Zucherman et al. |
| 2006/0241610 A1 | * | 10/2006 | Lim et al. ................ 606/69 |
| 2006/0241757 A1 | * | 10/2006 | Anderson ................ 623/17.11 |

FOREIGN PATENT DOCUMENTS

| | | |
|---|---|---|
| EP | 0 140 790 | 5/1985 |
| EP | 84308681.0 | 6/1985 |
| EP | 0322 334 | 6/1989 |
| WO | WO 91/16018 | 10/1991 |

OTHER PUBLICATIONS

Wheeles Textbook of Orthopaedics, Posterior Atlanto-Axial Arthrodesis Oct. 17, 2002 (1 pg).

(Continued)

*Primary Examiner*—Thomas C Barrett
*Assistant Examiner*—Nicholas Woodall
(74) *Attorney, Agent, or Firm*—Jeffrey A. Proehl; Woods, Fuller, Shultz & Smith PC

(57) ABSTRACT

A posterior cervical vertebral stabilizing system is disclosed. The system includes a device comprising an upper portion for positioning adjacent to a relatively superior vertebra of a patient's spine and a lower portion for positioning adjacent to a relatively inferior vertebra of the patient's spine. The upper portion forms a support for abutting the posterior surface of the superior vertebra and the lower portion forms a saddle for engaging a spinous process of the inferior vertebra. The device has an anterior face that, at each of the upper and lower portions, has a radius of curvature about an axis. The system includes a method of affixing the device to a spine of a patient by positioning the device posteriorly of the relatively superior and relatively inferior vertebrae, and looping cable about the device and the lamina of the vertebrae. The method may also include promoting fusion of the vertebrae together.

21 Claims, 6 Drawing Sheets

OTHER PUBLICATIONS

Wheeles Textbook of Orthopaedics, Dens Fracture Oct. 17, 2002 (2pgs).
Wheeles Textbook of Orthopaedics, Type 2 Dens Frx Oct. 17, 2002 (2pgs).
Johnson &Johnson, Codman TI-FRAME For Posterior Cervical Stabilization (1 pg).
Johnson & Johnson, Codman TI-FRAME Posterior Cervical Stabilization System Technique Guide (15 pgs).

* cited by examiner

POSTERIOR CERVICAL VERTEBRAL STABILIZING SYSTEM

BACKGROUND OF THE INVENTION

1. Field of the Invention

The present invention relates to spinal stabilization systems and more particularly pertains to a new posterior cervical vertebral stabilizing system including an apparatus and a method of employing the apparatus for not only stabilizing adjacent vertebrae with respect to each other, but also optionally facilitating fusion of the adjacent vertebrae.

2. Description of the Prior Art

Serious types of fractures of the vertebra of the spinal column of the human body include a fracture at the interface between the first cervical (C1) vertebra, or "atlas", and the second cervical (C2) vertebra, or "axis". The C2 vertebra includes an upstanding protrusion referred to as the odontoid process, or dens, about which the generally annular C1 vertebra extends. A fracture of the odontoid process, and especially a type two fracture of the odontoid process, is often treated by posterior atlanto-axial arthrodesis, which generally is intended to stabilize the C1 and C2 vertebrae with respect to each other and promote fusion of the vertebrae.

Known techniques for treating such fractures include internal stabilization of the C1 and C2 vertebra with respect to each other, using posterior C1-C2 transarticular facet screw fixation, which carries with it the risk of injury to the vertebral artery or the spinal cord. Another approach for treating such fractures is through interspinous wiring with interposition of a bone graft, which carries with it a high incidence of pseudoarthrosis, or non-healing of the bone employed for fusion.

In these respects, the posterior cervical vertebral stabilizing system according to the present invention substantially departs from the conventional concepts and designs and techniques of the prior art.

SUMMARY OF THE INVENTION

In view of the foregoing disadvantages inherent in the known types of spinal stabilization systems now present in the prior art, the present invention provides a new posterior cervical vertebral stabilizing system that can be utilized not only for stabilizing adjacent vertebrae with respect to each other, but also for facilitating fusion of the adjacent vertebrae.

To attain this, the present invention generally comprises a posterior cervical vertebral stabilizing system that has both apparatus and method aspects. In the apparatus aspect of the invention, a posterior cervical vertebral stabilizing device comprises an upper portion for positioning adjacent to a relatively superior vertebra of a patient's spine and a lower portion for positioning adjacent to a relatively inferior vertebra of the patient's spine. The upper portion forms a support for abutting the posterior surface of the superior vertebra and the lower portion forms a saddle for engaging a spinous process of the inferior vertebra. The device has an anterior face that, at each of the upper and lower portions, has a radius of curvature about an axis. In one highly preferred embodiment of the device, the radius of curvature of the anterior face at the upper portion is larger than the radius of curvature of the anterior face at the lower portion.

In the method aspect of the invention, the device is affixed to a spine of a patient by positioning the device posteriorly of the relatively superior and relatively inferior vertebrae, and looping cable about the device and the lamina of the vertebrae. The method may also include promoting fusion of the vertebrae together by harvesting cancellous bone from the patient's body, applying the harvested cancellous bone over the exposed lateral masses of the relatively superior and relatively inferior vertebrae, placing the harvested cancellous bone between the spinous processes and lamina of the inferior vertebra and the posterior arch of the superior vertebra, and placing the harvested cancellous bone in the aperture of the device.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

One significant advantage of the present invention is the intimate relationship that is possible between the device and the surfaces of the vertebrae to thereby form a very stable construct on the vertebrae, so that cancellous bone placed on and about the vertebrae and the device has a high likelihood of forming a successful fusion of the vertebrae.

Further advantages of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein.

DESCRIPTION OF PREFERRED EMBODIMENTS

Figure 1:
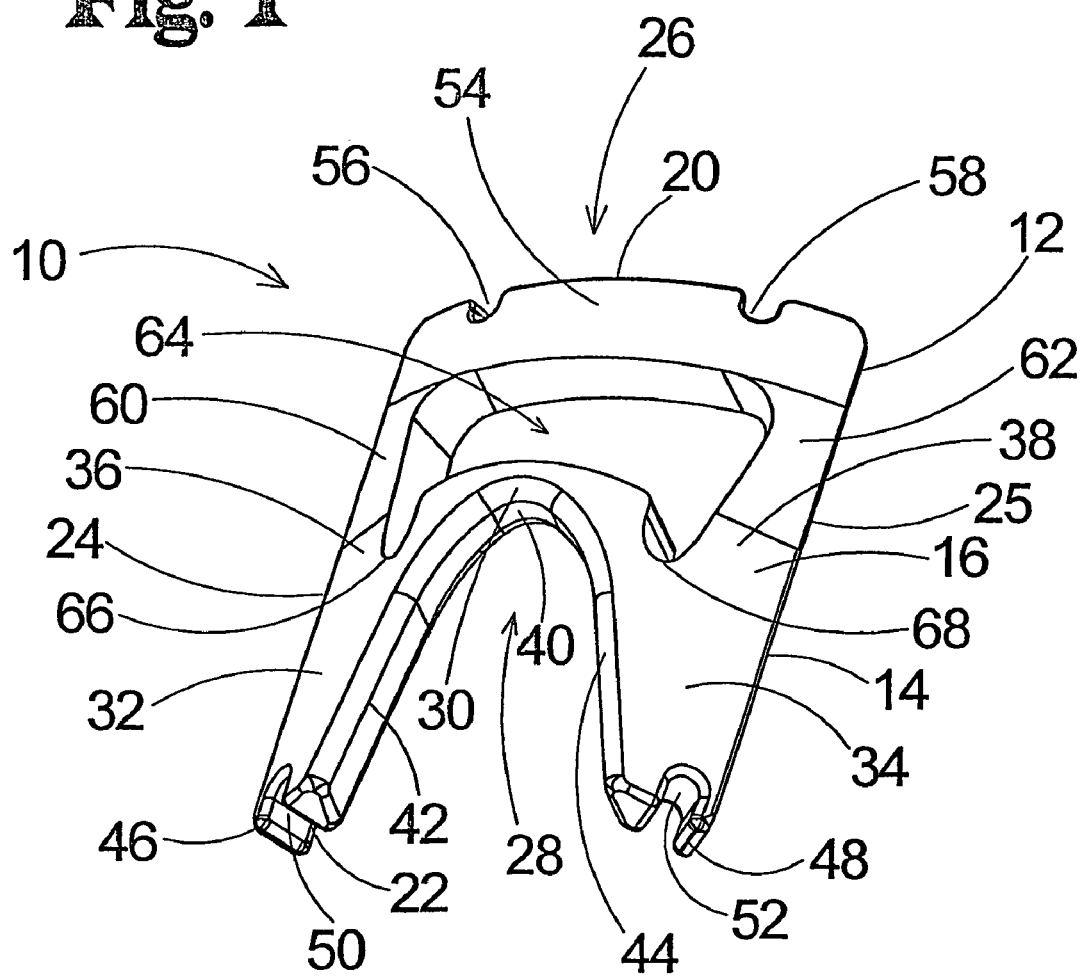
FIG. 1 is a schematic perspective view of the new posterior cervical vertebral stabilizing device according to the present invention.
Figure 2:
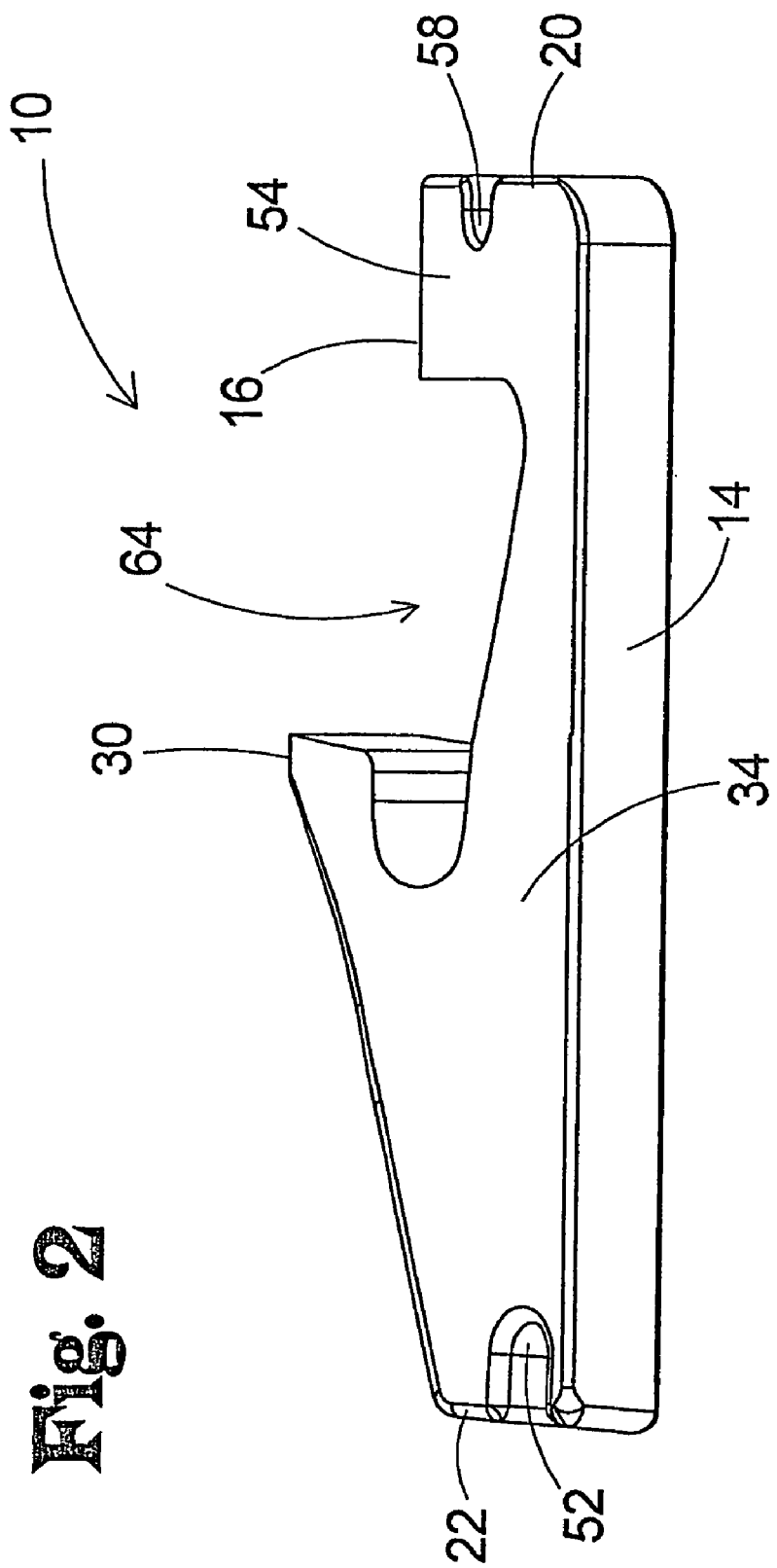
FIG. 2 is a schematic side view of posterior cervical vertebral stabilizing device of the present invention.

With reference now to the drawings, and in particular to FIGS. 1 through 6 thereof, a new posterior cervical vertebral stabilizing system embodying the principles and concepts of the present invention will be described.

As best illustrated in FIGS. 1 through 6, the posterior cervical vertebral stabilizing system of the invention includes a posterior cervical vertebral stabilizing device 10 for mounting on adjacent vertebrae of the spine of the patient, and the system of the invention also includes a method of utilizing the device 10 to stabilize the adjacent vertebrae with respect to each other.

The posterior cervical vertebral stabilizing device 10 of the invention is highly suitable for stabilizing adjacent vertebrae with respect to each other. In one embodiment, the device 10 comprises an upper portion 12 which may be positioned adjacent to a relatively superior vertebra 2 of a patient's spine 1, and also includes a lower portion 14 which may be positioned adjacent to a relatively inferior vertebra 4 of the patient's spine (see FIGS. 5 and 6).

The device 10 has a posterior face 16 for positioning away from the spine of the patient, and an anterior face 18 for positioning toward and adjacent to the patient's spine. The anterior face 18 of the device 10 may be curved or generally concave in shape for following, to a significant degree, the curvature of the superior 2 and inferior 4 vertebrae. In one preferred embodiment of the invention, the anterior face 18 at the upper portion 12 of the device has a greater or more severe curvature than the anterior face at the lower portion 14 of the device. In such an embodiment, the anterior face 18 has a radius of curvature at each of the upper 12 and lower 14 portions. The radius of curvature of the upper portion 12 may be greater, or relatively longer, than the radius of curvature of the lower portion 14 (see FIG. 3), which is relatively shorter. Significantly, the concavity or relative curvature of the upper portion 12 may be of a relatively lesser or smaller degree in order to conform better and more intimately to the posterior arch of the C1 vertebra, and the concavity or relative curvature of the lower portion 14 may be of a relatively greater degree in order to conform better and more intimately to the lamina of the C2 vertebra.

The device 10 of the invention has a top 20 for orienting upwardly on the patient and a bottom 22 for orienting downwardly on the patient. The device 10 also has lateral sides 24, 25 that extend between the top 20 and bottom 22, and the lateral sides may be oriented substantially parallel to each other. The upper portion 12 of the device 10 may form a support 26 for abutting or resting against the posterior surface 3 of the relatively superior vertebra 2, and the lower portion 14 may form a saddle 28 for positioning adjacent to, and optionally engaging, the spinous process 6 or posterior protrusion of the relatively inferior vertebra 4.

The lower portion 14 of the device 10 may form an arch 30 for positioning substantially superiorly to and about a portion of the spinous process 6 of the relatively inferior vertebra. The lower portion 14 may include a pair of legs 32, 34 for positioning on opposite sides of the spinous process 6 of the relatively inferior vertebra, and the arch 30 may extend substantially transversely between the respective upper sections 36, 38 of the legs 32, 34. The arch 30 may have an inferior surface 40, and each of the legs 32, 34 may have a respective inner edge 42, 44. The inner edges 42, 44 of the legs may converge toward each other in a superior or upward direction when positioned for implantation in the body, and may diverge away from each other in an inferior or downward direction. Each of the legs 32, 34 may have a respective distal tip section 46, 48.

Figure 3:
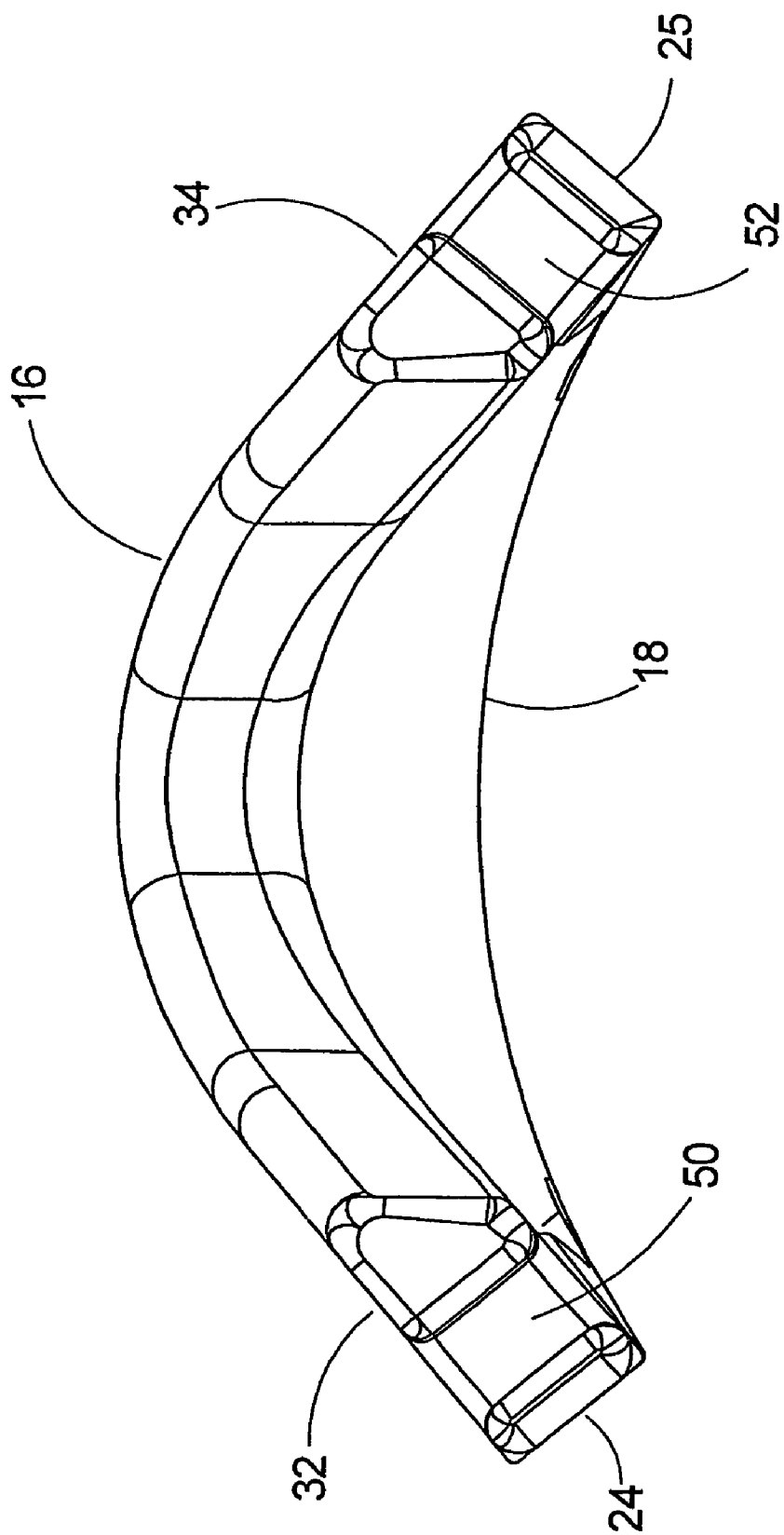
FIG. 3 is a schematic bottom end view of posterior cervical vertebral stabilizing device of the present invention.
Figure 4:
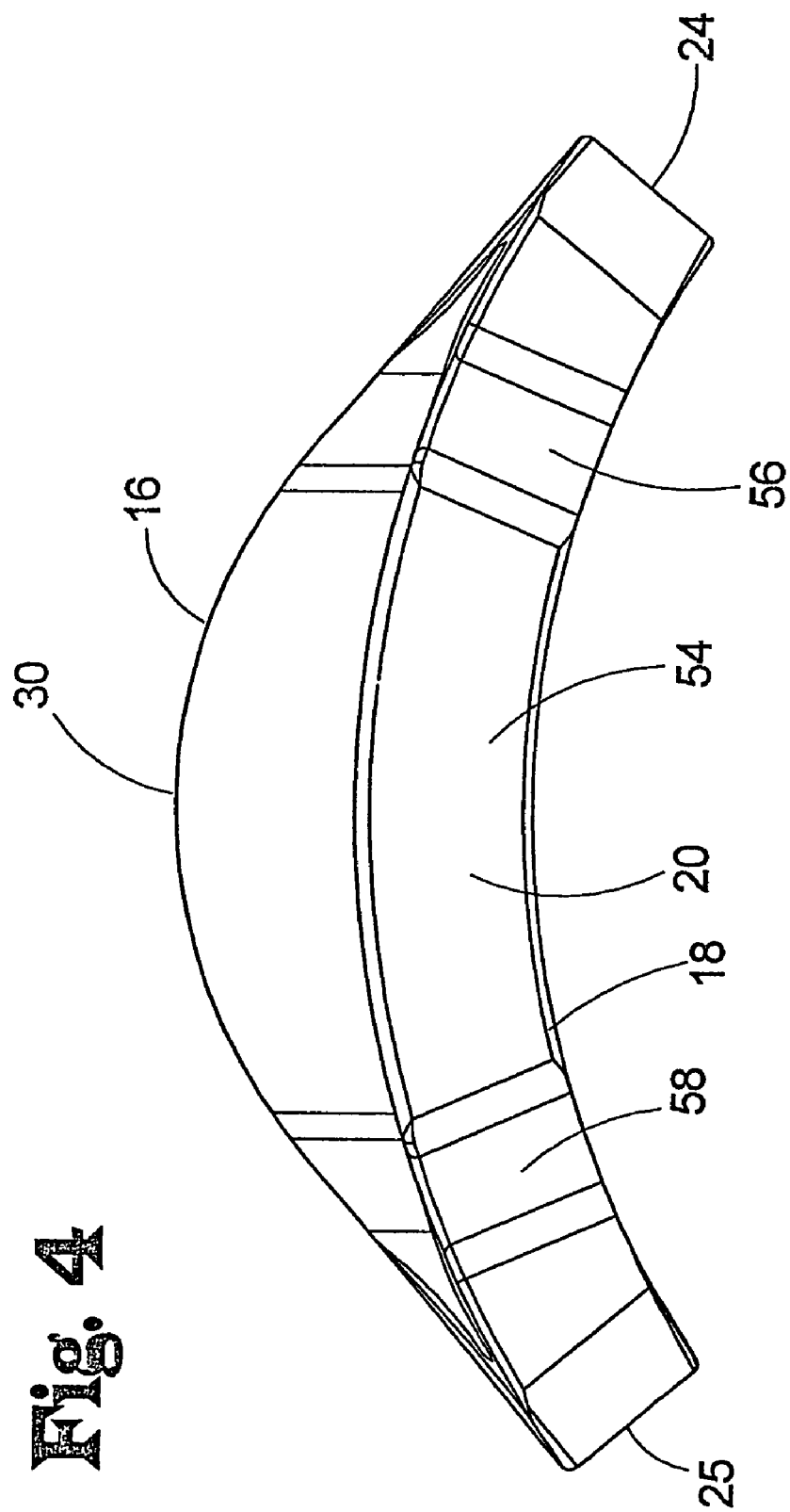
FIG. 4 is a schematic top end view of posterior cervical vertebral stabilizing device of the present invention.

The curvature of the anterior face 18 of the device 10 described above may be such that a portion of the anterior face on the leg 32 is oriented at an angle to a portion of the anterior face on the of the leg 34 (see, e.g., FIG. 3). The angle may be in the range of approximately 80 degrees to approximately 120 degrees, and in one embodiment measures approximately 90 degrees The upper portion 12 of the device 10 may have a bridge 54 that extends between the lateral sides 24, 25. The upper portion 12 may also have a pair of lateral side extents 60, 62, with each of the lateral side extents extending between one of the legs 32, 34 and the bridge 54. The bridge 54, the arch 30, and the lateral side extents 60, 62 may define an interior aperture 64 therebetween.

To provide for a more secure mounting of cables on the device in a manner that resists lateral slippage, a number of grooves or notches may be provided on the device 10. The bridge 54 may have a cable-receiving groove, and may have a pair of grooves 56, 58, that extend from the anterior face 18 to the posterior face 16 of the device 10. Further, each distal tip section 46, 48 of a respective leg may have a respective cable-receiving groove 50, 52 formed therein that extends from the anterior face 18 to the posterior face 16. Still further, the lower portion 14 may have a notch 66, 68 positioned in an upper section of each of the respective legs 32, 34, and each of the notches may be in communication with the aperture 64.

It should be realized that the device 10 of the invention may be relatively elongated from top 20 to bottom 22 to a greater degree to permit extension of the device between three, four, or even more vertebrae of the spinal column for stabilizing three, four, or more vertebrae with respect to each other, and optionally for fusion of the three, four, or more vertebrae.

Another aspect of the system of the invention is a method of performing a posterior atlanto-axial arthrodesis that may most suitably be performed using the posterior vertebral stabilizing device of the system.

Figure 5:
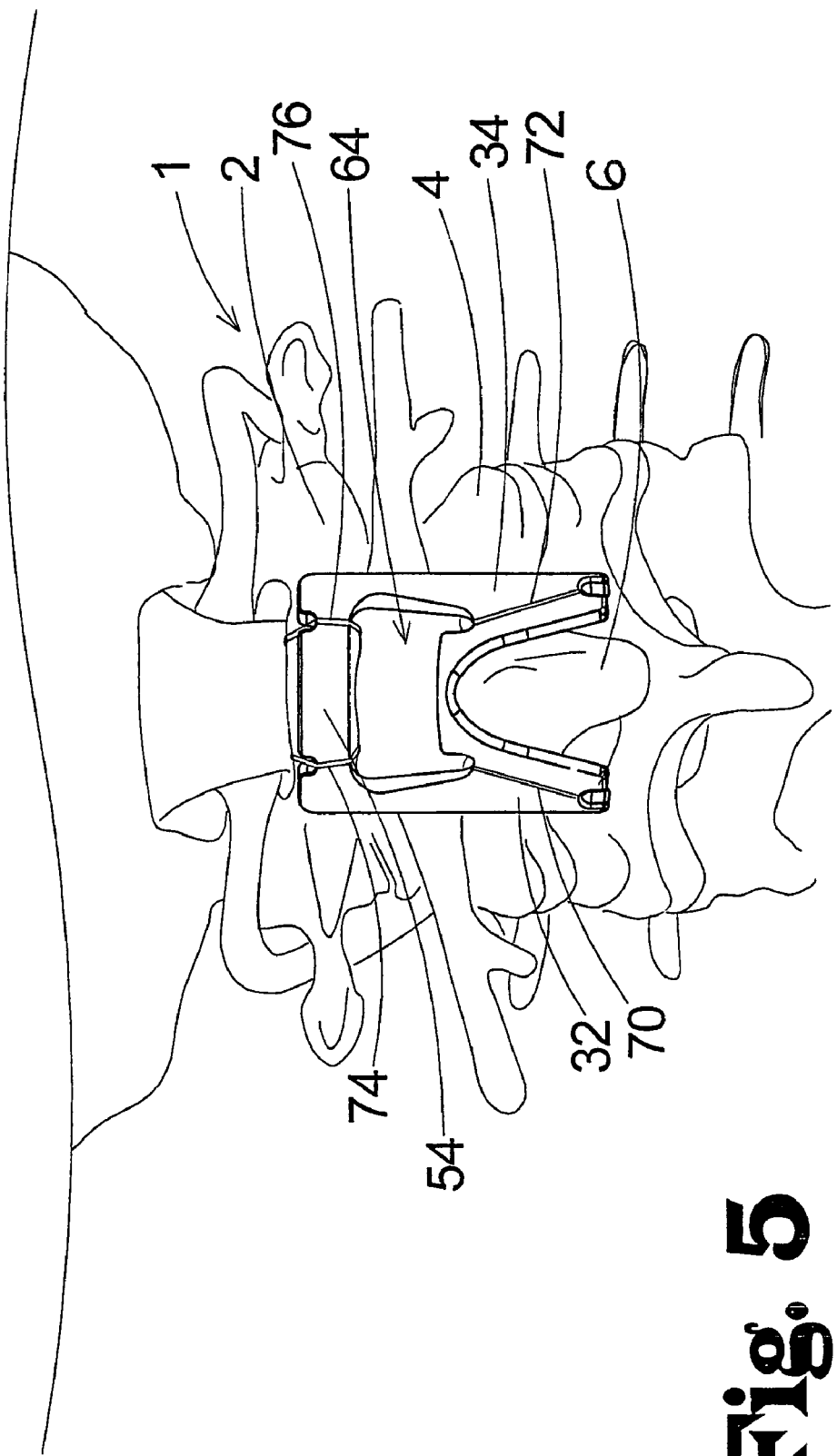
FIG. 5 is a schematic posterior view of the device of the present invention shown mounted on the superior and inferior vertebrae of the spine.
Figure 6:
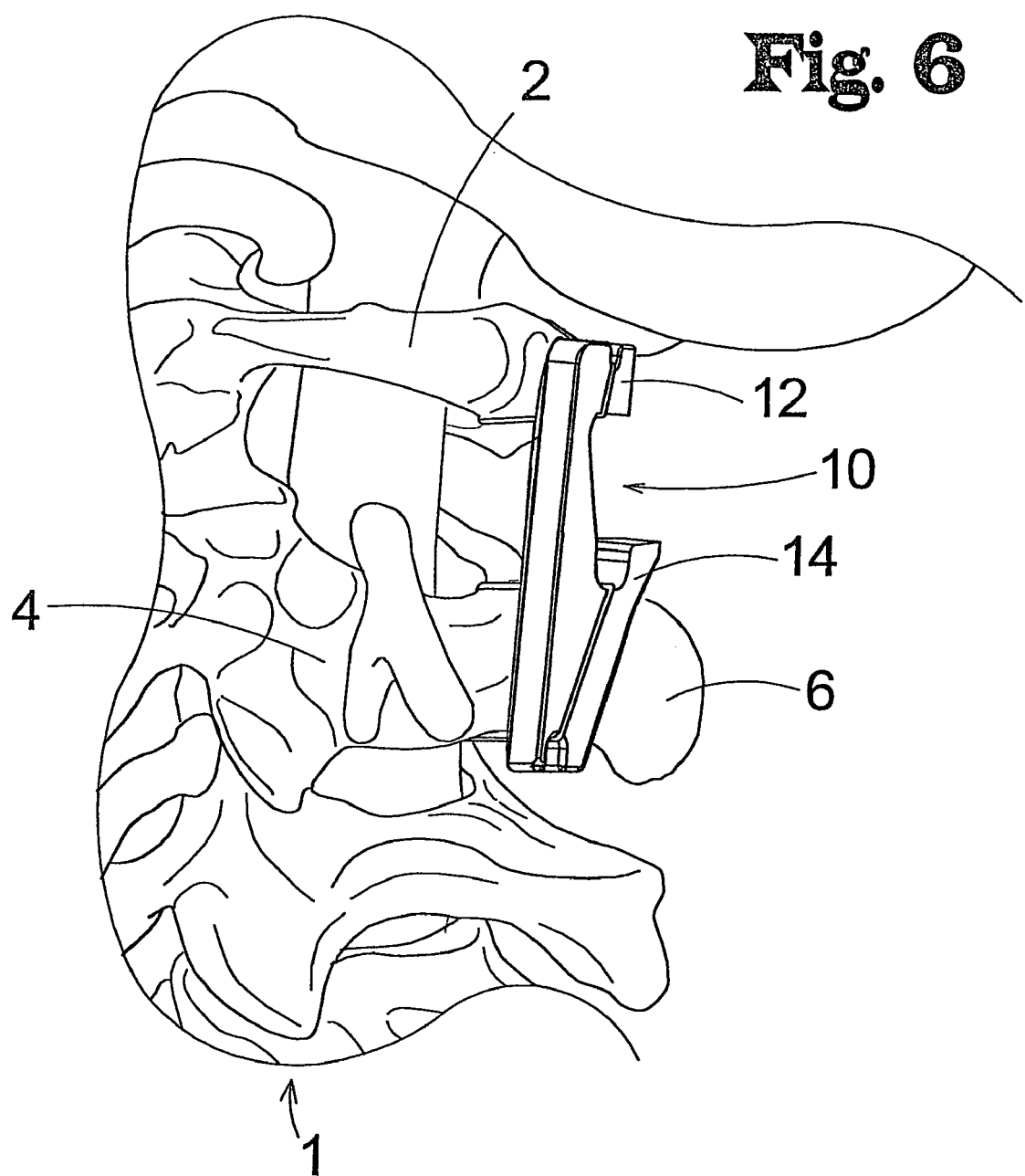
FIG. 6 is a schematic lateral view of the device of the present invention shown mounted on the superior and inferior vertebrae of the spine.

In performing the method of the invention, the posterior cervical vertebral stabilizing device 10 is affixed to the spine 1 of a patient. The device 10 may be positioned posteriorly of the relatively superior vertebra 2 and the relatively inferior vertebra 4 of the spine 1, and may be abutted against the posterior surfaces of the relatively superior and relatively inferior vertebra. In the most preferred practice of the invention, the device is attached to the first cervical (C1) vertebra, or atlas, and the second cervical (C2) vertebra, or axis, for stabilizing, and preferably fusing, these vertebrae with respect to each other. The bridge 54 of the device 10 is positioned posteriorly of the posterior arch of the C1 vertebra, and may extend about the posterior tubercle of the C1 vertebra. Similarly, the lower portion 14 of the device 10, including the arch 30 and the legs 32, 34, is positioned posteriorly of the lamina of the C2 vertebra, with the legs being positioned on either side of the spinous process 6. As can be seen in FIG. 5, the arch 30 and legs 32, 34 of the device may embrace and surround a significant portion of the spinous process of the C2 vertebra, and the bridge 54 extends along (in a generally parallel fashion) a portion of the posterior arch of the C1 vertebra. The curvature of the anterior face 18 of the device 10 facilitates the positioning and the abutment of the device in a close and intimate relationship with the posterior surfaces of the vertebrae.

The affixation of the device to the vertebrae of the spinal column may be performed by looping an elongate flexible member, such as stainless steel or titanium cable, about portions of the device and portions of the vertebrae 2, 4 (see FIG. 5). In one preferred practice of the method of the invention, four lengths 70, 72, 74, 76 of cable are looped about portions of the device and portions of the vertebra. A first length 70 of cable may be looped about the device 10 and the lamina of the relatively inferior vertebra 4, and the first length may be extended through the cable-receiving groove 50 and the notch 66 of the first leg 32. Similarly, a second length 72 of cable may be looped about the device 10 and the relatively inferior vertebra 4 with the second length being extended through the cable-receiving groove 52 and the notch 68 of the second leg 34.

A third length 74 of cable may be looped about the device 10 and the lamina of the relatively superior vertebra 2, and the third length may be extended through the cable-receiving groove 56 of the bridge 54 of the device. Similarly, a fourth length 76 of cable may be looped about the device 10 and the lamina of the relatively superior vertebra 2 with the third length extended through the cable-receiving groove 58 of the bridge 54 of the device.

The method of the system may also include the promotion of fusion of the relatively superior vertebra 2 to the relatively inferior vertebra 4. Bone material may be harvested from the patient's body, such as cancellous bone taken from the iliac crest of the patient. The harvested cancellous bone may be applied over the exposed lateral masses of the relatively superior and relatively inferior vertebrae, and may also be placed between the spinous processes and lamina of the inferior vertebra 4 and the posterior arch of the superior vertebra 6. The harvested cancellous bone may also be placed in the aperture 64 of the device 10 mounted on the vertebral column.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A posterior cervical vertebral stabilizing device for stabilizing adjacent first cervical (C1) and second cervical (C2) vertebrae with respect to each other in the spine of a patient, the device comprising:

a top and a bottom and lateral sides extending between the top and bottom;

an upper portion for positioning adjacent to the C1 vertebra located relatively superior in a patient's spine and a lower portion for positioning adjacent to the C2 vertebra located relatively inferior in the patient's spine, the upper portion forming a support for abutting the posterior surface of the C1 vertebra and the lower portion forming a saddle for engaging a spinous process of the C2 vertebra; and a posterior face and an anterior face, the anterior face being positionable adjacent to the C1 and C2 vertebrae of the spine;

wherein the lateral sides define a plane and the upper portion and the lower portion both extend in a posterior direction from the plane, the anterior face of the lower portion extending further in a posterior direction from the plane than the anterior face of the upper portion.

2. The posterior cervical vertebral stabilizing device of claim 1 wherein the anterior face of the upper portion has a radius of curvature greater than a radius of curvature of the anterior face of the lower portion.

3. The posterior cervical vertebral stabilizing device of claim 1 wherein the lower portion includes a pair of legs for positioning on opposite sides of the spinous process of the C2 vertebra, and wherein each of the legs has an inner edge, the inner edges of the legs converging toward each other toward the top and diverging away from each other toward the bottom.

4. The posterior cervical vertebral stabilizing device of claim 1 wherein the lower portion has an arch for positioning superiorly to the spinous process of the C2 vertebra.

5. The posterior cervical vertebral stabilizing device of claim 4 wherein the arch having an inferior surface for resting on the spinous process of the C2 vertebra.

6. The posterior cervical vertebral stabilizing device of claim 1 wherein the lower portion includes a pair of legs for positioning on opposite sides of the spinous process of the C2 vertebra, and wherein the lower portion has an arch for positioning superiorly to the spinous process of the C2 vertebra, the arch extending substantially transversely between upper sections of the legs.

7. The posterior cervical vertebral stabilizing device of claim 1 wherein the lower portion includes a pair of legs for positioning on opposite sides of the spinous process of the C2 vertebra, and wherein each of the legs has a distal tip section, each of the distal tip sections having a cable-receiving groove extending from the anterior face to the posterior face.

8. The posterior cervical vertebral stabilizing device of claim 1 wherein the upper portion has a bridge extending between the lateral sides.

9. The posterior cervical vertebral stabilizing device of claim 8 wherein the bridge has a cable-receiving groove extending from the anterior face to the posterior face.

10. The posterior cervical vertebral stabilizing device of claim 1 wherein the lower portion includes a pair of legs for positioning on opposite sides of the spinous process of the C2 vertebra, wherein the upper portion has a bridge extending between the lateral sides, and wherein the upper portion has a pair of lateral side extents, each of the lateral side extents extending between one of the legs and the bridge.

11. The posterior cervical vertebral stabilizing device of claim 10 wherein the lower portion has an arch for positioning superiorly to the spinous process of the C2 vertebra, and wherein the bridge, the arch, and the lateral side extents forming an interior aperture therebetween.

12. The posterior cervical vertebral stabilizing device of claim 11 wherein the lower portion has a notch positioned in an upper section of each of the legs, each of the notches being in communication with the aperture.

13. The posterior cervical vertebral stabilizing device of claim 1 wherein the anterior face of the upper portion has a radius of curvature greater than a radius of curvature of the anterior face of the lower portion;

wherein the lateral sides define a plane, a center portion of the anterior face of the lower portion extending further from the plane than a center portion of the anterior face of the upper portion;

wherein the lower portion includes a pair of legs for positioning on opposite sides of the spinous process of the C2 vertebra;

wherein each of the legs has an inner edge, the inner edges of the legs converging toward each other toward the top and diverging away from each other toward the bottom;

wherein the lower portion has an arch for positioning superiorly to the spinous process of the C2 vertebra;

wherein the arch having an inferior surface for resting on the spinous process of the C2 vertebra;

wherein the lower portion has an arch for positioning superiorly to the spinous process of the C2 vertebra, the arch extending substantially transversely between upper sections of the legs;

wherein each of the legs has a distal tip section, each of the distal tip sections having a cable-receiving groove extending from the anterior face to the posterior face;

wherein the upper portion has a bridge extending between the lateral sides;

wherein the bridge has a cable-receiving groove extending from the anterior face to the posterior face;

wherein the lower portion includes a pair of legs for positioning on opposite sides of the spinous process of the C2 vertebra, wherein the upper portion has a bridge extending between the lateral sides, and wherein the upper portion has a pair of lateral side extents, each of the lateral side extents extending between one of the legs and the bridge;

wherein the bridge, the arch, and the lateral side extents forming an interior aperture therebetween;

wherein the lower portion has a notch positioned in an upper section of each of the legs, each of the notches being in communication with the aperture; and wherein the top is substantially straight between the lateral sides.

14. The posterior cervical vertebral stabilizing device of claim 1 wherein the lateral sides define a plane, a center portion of the anterior face of the lower portion extending further in an anterior direction from the plane than a center portion of the anterior face of the upper portion.

15. The posterior cervical vertebral stabilizing device of claim 1 wherein the top includes a section between the lateral sides that is straight.

16. A method of posterior atlanto-axial arthrodesis for the first cervical (C1) and second cervical (C2) vertebrae, the method comprising:

providing a posterior cervical vertebral stabilizing device comprising:

a top and a bottom and lateral sides extending between the top and bottom;

an upper portion for positioning adjacent to the C1 vertebra located relatively superior in a patient's spine and a lower portion for positioning adjacent to the C2 vertebra located relatively inferior in the patient's spine, the upper portion forming a support for abutting the posterior surface of the C1 vertebra and the lower portion forming a saddle for engaging a spinous process of the C2 vertebra; and a posterior face and an anterior face, the anterior face being positionable adjacent to the C1 and C2 vertebrae of the spine, the lateral sides define a plane, the upper portion and the lower portion both extending in a posterior direction from the plane, a center portion of the anterior face of the lower portion extending further in a posterior direction from the plane than a center portion of the anterior face of the upper portion; and affixing the posterior cervical vertebral stabilizing device to the C1 and C2 vertebrae of the spine of a patient, comprising:

positioning the anterior face of the upper portion of the device posteriorly of the relatively superior C1 vertebra and the anterior face of the lower portion of the device posteriorly of the relatively inferior C2 vertebra; and looping cable about the portions of the device and portions of lamina of the C1 and C2 vertebrae.

17. The method of claim 16 wherein further including the step of promoting fusion which comprises:

harvesting cancellous bone from the patient's body;

applying the harvested cancellous bone over the exposed lateral masses of the relatively superior and C2 vertebrae;

placing the harvested cancellous bone between the spinous processes and lamina of the C2 and the posterior arch of the C1 vertebra; and placing the harvested cancellous bone in the aperture of the device.

18. The method of claim 16 wherein the step of looping cable includes:

looping a first length of cable about the device and the lamina of the C2 vertebra;

looping a second length of cable about the device and the lamina of the C2 vertebra;

looping a third length of cable about the device and the lamina of the C1 vertebra; and looping a fourth length of cable about the device and the lamina of the C2 vertebra.

19. The method of claim 18 wherein the first length extends through a cable-receiving groove of one of the legs of the device, the second length extends through the cable-receiving groove of one of the legs of the device, the third length extends through the cable-receiving groove of the bridge of the device, and the fourth length extends through the cable-receiving groove of the bridge of the device.

20. A posterior cervical vertebral stabilizing device for stabilizing adjacent first cervical (C1) and second cervical (C2) vertebrae with respect to each other in the spine of a patient, the device comprising:

a top and a bottom and lateral sides extending between the top and bottom;

a posterior face and an anterior face, the anterior face being positionable adjacent to the C1 and C2 vertebrae of the patient's spine;

an upper portion located toward the top and configured for positioning adjacent to the C1 vertebra located relatively superior in a patient's spine;

a lower portion located toward the bottom and configured for positioning adjacent to the C2 vertebra located relatively inferior in the patient's spine;

wherein the upper portion forms a support abuttable against the posterior surface of the relatively superior C1 vertebra;

wherein the lower portion forms a saddle engagable with a spinous process of the relatively inferior C2 vertebra;

wherein the lateral sides define a plane and the upper portion and the lower portion both extend in a posterior direction from the plane;

wherein the lower portion extends further in posterior direction from the plane of the lateral sides than the upper portion such that the upper portion is abuttable against the posterior surface of a posterior arch of the C1 vertebra while the lower portion is abuttable against a posterior surface of a lamina of the C2 vertebra as the saddle of the lower portion engages the spinous process of the C2 vertebra.

21. The posterior cervical vertebral stabilizing device of claim 20 wherein a furthest extent of the lower portion in the posterior direction is greater than a furthest extent of the upper portion in the posterior extent.

* * * * *